United States Patent [19]

Riepl et al.

[11] Patent Number: 5,098,978
[45] Date of Patent: Mar. 24, 1992

[54] LIQUID-CRYSTALLINE POLYMERS CONTAINING CHROMOPHORIC SIDE GROUPS

[75] Inventors: Georg Riepl, Burghausen; Franz-Heinrich Kreuzer; Alfred Miller, both of Martinsried, all of Fed. Rep. of Germany

[73] Assignee: Consortium fur elektrochemisch Ind. GmbH, Munich, Fed. Rep. of Germany

[21] Appl. No.: 318,391

[22] Filed: Mar. 3, 1989

[30] Foreign Application Priority Data

Mar. 14, 1988 [DE] Fed. Rep. of Germany ....... 3808430

[51] Int. Cl.⁵ .................... C08G 77/26; C08G 77/08
[52] U.S. Cl. ........................................ 528/15; 528/25; 528/26; 528/28; 528/31; 525/479; 428/1
[58] Field of Search ............... 528/15, 25, 26, 28, 528/31; 525/479; 428/1

[56] References Cited

U.S. PATENT DOCUMENTS

| | | | |
|---|---|---|---|
| 4,388,453 | 6/1983 | Finkelmann et al. | 528/15 |
| 4,410,570 | 10/1983 | Kreuzer et al. | 427/374.1 |
| 4,631,328 | 12/1986 | Ringsdorf et al. | 526/259 |
| 4,713,196 | 12/1987 | Praefcke et al. | 252/299.01 |
| 4,730,904 | 3/1988 | Pauluth et al. | 350/340 |
| 4,774,028 | 9/1988 | Imai et al. | 260/397.2 |
| 4,865,762 | 9/1989 | Kreuder et al. | 528/25 |
| 4,868,250 | 9/1989 | De Martino et al. | 525/479 |
| 4,943,617 | 7/1990 | Etzbach et al. | 525/329.9 |

OTHER PUBLICATIONS

"Investigations of Smectic Polysiloxanes 3–Ultra High Contrast Smectic Polymer Storage Effect", Molecular Crystals and Liquid Crystals Letters, vol. 3/4, Coles et al., (1985).

Primary Examiner—John C. Bleutge
Assistant Examiner—R. Dean, Jr.

[57] ABSTRACT

The invention relates to cholesteric organic polymers which contain, in the side groups, both mesogens, at least some of which are optically active, and chromophoric groups.

26 Claims, No Drawings

LIQUID-CRYSTALLINE POLYMERS CONTAINING CHROMOPHORIC SIDE GROUPS

The invention relates to cholesterically liquid-crystalline organic polymers containing chromophoric side groups.

BACKGROUND OF THE INVENTION

Cholesterically liquid-crystalline organopolysiloxanes and their preparation are disclosed, inter alia, in U.S. Pat. No. 4,410,570 to Kreuzer et al. Nematically liquid-crystalline polyacrylates which, in addition to mesogenic groups, also contain chromophoric groups in the side chains are described by H. Ringsdorf and H. W. Schmidt [Makromol. Chem. 187, 1327-1334 (1984)].

Therefore, it is an object of the present invention to provide cholesteric organic polymers, preferably organopolysiloxanes, which can be easily oriented. A further object of the present invention is to provide cholesteric organic polymers, preferably organopolysiloxanes, whose orientation can be eliminated or modified at certain points by the incidence of light.

SUMMARY OF THE INVENTION

The foregoing objects and others which will become apparent from the following description are accomplished in accordance with this invention, generally speaking, by providing cholesterically liquid-crystalline organic polymers, particularly organopolysiloxanes, which contain in the side groups, both mesogens, at least some of which are optically active, and chromophoric groups.

DESCRIPTION OF THE INVENTION

Chromophoric groups mean groups which absorb electromagnetic radiation in a wavelength range of from 200 nm to 800 nm. Examples of chromophoric groups are, in particular, groups containing azo, azoxy, anthraquinone, stilbene, imine and polymethine functions. Polymers, in particular organopolysiloxanes, which contain azo or azoxy groups as chromophoric groups are preferred.

The ability of liquid-crystalline phases to be readily oriented is very essential for the utility of such compounds. The simplicity of orienting liquid-crystalline phases is, therefore, an essential criterion for the usability of these materials.

Suitable mesogens are all known mesogenic groups. At least some of these optically active mesogens must be sufficiently high so that a cholesteric phase can be produced. These are, in particular, mesogenic groups described by D. Demus et al. ["Flüssige Kristalle in Tabellen" (Liquid Crystals in Tables), Deutscher Verlag für Grundstoffindustrie, Leipzig, Volume I (1974) and Volume II (1984)].

The polymers, according to this invention, can, in particular, be those whose backbone comprises oligomers or polymers of acrylates, methacrylates, organosiloxanes, esters, ethers, alkenes, amides and sulfones, preferably oligomers or polymers of organosiloxanes.

The organopolysiloxanes of this invention are, in particular, those which are built up from units of the formula

 (I).

where R represents the same or different monovalent radicals of the formula

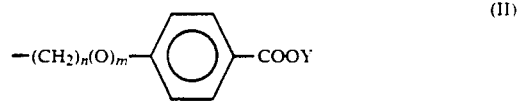 (II)

in which n represents an integer having a value of from 2 to 12, and more preferably 2, 3 or 4; m represents an integer having a value of 0 or 1; and Y represents either the same or different phenyl radicals which are substituted in the paraposition by a halogen, cyano, $C_1$- to $C_8$-alkoxy, phenyl, phenoxy or cyclohexyl radical or a cholesteryl, 4-cyclohexyl-cyclohexyl or pinan-10-yl radical; R' represents the same or different monovalent radical of the formula $$-(CH_2)_n(O)_m-Z \qquad (III)$$

in which n and m are as defined above, and Z is a radical of the formula

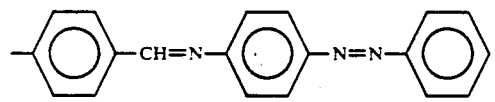

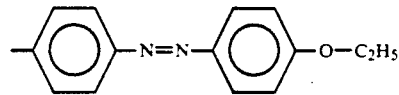

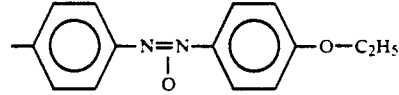

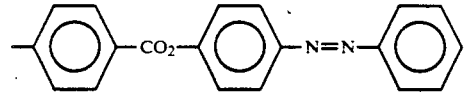

R" represents the same or different $C_1$-to $C_8$-alkyl radicals or phenyl radical, which may be substituted by halogen atoms, and a, b and c in each case represent integers having a value of from 0 to 3, with the proviso that the sum of a, b and c is a maximum of 3 and, on the average, each organopolysiloxane molecule contains at least one unit of the formula (I) for which a has a value of at least 1 and one for which b has a value of at least 1.

It is particularly preferred for the organopolysiloxanes of this invention to be built up from units of the formulas

 (VIII),

 (IX)

and optionally

 (X)

in which R, R', R", a, b and c are the same as in formula (I).

Preferred radicals represented by R" in formulas (I) and (VIII), (IX) and (X) are the same or different methyl, ethyl or phenyl radicals and in particular methyl radicals.

Of the organopolysiloxanes of this invention, essentially straight-chain organopolysiloxanes are particularly preferred, i.e., those compounds of the formulas above in which the sum of a+b+c has an average value of from 1.8 to 2.2, and more preferably from 1.9 to 2.1.

The organopolysiloxanes of this invention preferably have a mean molecular weight of at least 1,200 atomic mass units.

The organopolysiloxanes of this invention can be prepared by processes known heretofore. Thus, in particular, organopolysiloxanes built up from siloxane units of formula (I) can be prepared by reacting organopolysiloxanes containing hydrogen atoms bonded directly to Si atoms, i.e., in particular, those of the formula

$$R''_c H_{(a+b)} SiO_{(4-a-b-c)/2} \qquad (XI).$$

with compounds of the formula

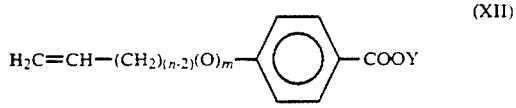

and compounds of the formula

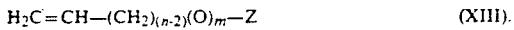

$$H_2C=CH-(CH_2)_{(n-2)}(O)_m-Z \qquad (XIII).$$

It is preferred that a equivalents of compounds of formula (XII) and b equivalents of compounds of formula (XIII) be employed. It is possible to employ one compound of each of formulas (XII) and (XIII), but it is also possible to employ several compounds of formulas (XII) and/or (XIII). It is possible to employ one or several compounds of formula (XI). A compound or compounds of formula (XI) may first be reacted with a compound or compounds of formula (XII) and then with a compound or compounds of the formula (XIII), or vice versa. A compound or compounds of formulas (XII) and (XIII) are preferably reacted in one step with a compound or compounds of formula (XI).

The meaning of n and m in formulas (II) and (XII) is in each case independent of their meaning in formulas (III) and (XIII).

The organopolysiloxanes of formulas (XI) may be straight-chain or cyclic. Examples of compounds of formula (XI) are dimethyl(poly)siloxanes having hydrogen atoms bonded directly to Si atoms in the end groups, and also optionally along the siloxane chain, cyclic siloxanes, such as trimethylcyclotrisiloxane, tetramethylcyclotetrasiloxane, pentamethylcyclopentasiloxane and the like. In the process of this invention, cyclosiloxanes of the formula $[(CH_3)HSiO]_x$, where x represents an integer having a value of from 3 to 8 are preferred.

The reactions mentioned above are preferably carried out in the presence of a catalyst. The catalysts employed are preferably platinum metals and/or compounds thereof, and more preferably platinum and/or compounds thereof. All catalysts which have also been employed heretofore for the addition reaction of hydrogen atoms bonded directly to Si atoms with aliphatically unsaturated compounds can be employed here. Examples of such catalysts are metallic and finely divided platinum, which may be supported on materials, such as silicon dioxide, aluminum oxide or activated charcoal, compounds or complexes of platinum, such as platinum halides, for example $PtCl_4$, $H_2PtCl_6.6H_2O$, $Na_2PtCl_4.4H_2O$, platinum-olefin complexes, platinum-alcohol complexes, platinum-alcoholate complexes, platinum-ether complexes, platinum-aldehyde complexes, platinum-ketone complexes, including products of the reaction of $H_2PtCl_6.6H_2O$ and cyclohexanone, platinum-vinylsiloxane complexes, in particular platinum-divinyltetramethyldisiloxane complexes with or without a content of detectable inorganically bonded halogen, bis-(gamma-picoline)-platinum dichloride, trimethylenedipyridineplatinum dichloride, dicyclopentadiene-platinum dichloride, (dimethyl sulfoxide)ethyleneplatinum(II) dichloride and products obtained from the reaction of platinum tetrachloride with an olefin and a primary amine or a secondary amine or a primary and a secondary amine, such as the product of the reaction of platinum tetrachloride, dissolved in 1-octene, with sec-butylamine, or ammonium-platinum complexes as described in EP-B 110,370.

Catalysts of the abovementioned type are generally used in amounts of from 1 ppm by weight to 1,000 ppm by weight, based on the weight of the compounds of formula (XI) employed.

The reaction is preferably carried out in a solvent. Examples of such solvents are hydrocarbons, such as pentane, hexane, petroleum ether, benzene, toluene and xylenes; halogenated hydrocarbons, such as dichloromethane, trichloromethane, tetrachloromethane, 1,1,1-trichloroethane, ethylene chloride, perchloroethylene, dichlorodifluoromethane and the like. The solvent is preferably toluene.

The reaction is preferably carried out at temperatures of from 0° C. to 200° C., and more preferably at temperatures of from 20°C. to 120° C.

The reaction can be carried out at the pressure of the ambient atmosphere, i.e., at about 0.1 MPa (abs.). Pressures of from 0.09 MPa (abs.) to 0.11 MPa (abs.) are preferred.

The reaction time depends, inter alia, on the reaction temperature and on the activity and amount of the catalyst used. It is generally between 20 minutes and 24 hours.

The organopolysiloxanes according to the invention can also be prepared by hydrolyzing compounds of the formula

$$R_a R'_b R''_c SiX_{(4-a-b-c)} \qquad (XIV),$$

where, in the abovementioned formula (XIV), X represents a halogen atom, a $C_1$-to $C_4$-alkoxy group or a hydroxyl group, and R, R', R", a, b and c are the same as defined in formula (I), with the proviso that the sum a+b+c has an average value of from 1.5 to 2.2.

The cholesterically liquid-crystalline organic polymers of this invention, i.e., in particular, organopolysiloxanes containing chromophoric side groups, can easily be oriented, i.e., their mesogenic side groups can easily be aligned in the same way. In contrast to customary polymeric liquid crystals, they can even be oriented, for example, by mechanical treatment, such as by shearing or by application by hand coaters. Of course, they can also be aligned by customary methods, such as by surface effects, or electrical or magnetic fields. A particular advantage of the organopolysiloxanes of this invention over other liquid crystals is that their orientation can be changed after they have been oriented by the incidence of light. Thus, for example, the refractive index of the oriented liquid-crystal layer can be altered by exposure to light. In this context, light is preferably taken to mean electromagnetic radiation in a wavelength range of from 200 nm to 800 nm, i.e., including ultra-violet light. This reorientation is in each case effected only on the area exposed to light. The organopolysiloxanes of this invention can thus be reoriented fully, but also on very small sub-areas. Through reorientation in very small regions, it is possible to employ the organopolysiloxanes of this invention as components of erasable information stores and as information carrier material. It is, of course, possible to use the organopolysiloxanes of this invention for all purposes for which cholesteric liquid crystals have heretofore also been employed.

In this description, formulas containing the -symbols "-o" or "-o-" without being surrounded by a hexagon, then the symbol -o is intended to represent a phenyl radical, -o- is intended to represent a paraphenylene radical.

In the examples below, all quantities are by weight, unless otherwise specified. Temperatures and pressures are about 23 C and 0.1 MPa (abs.), respectively, unless otherwise apparent from the context. The glass transition temperatures and clear points of the products of this invention were in each case determined by differential thermoanalysis (DTA).

EXAMPLE 1

About 0.5 ml of a 1 percent by weight solution of dicyclopentadiene-platinum dichloride in dichloromethane was added to a solution containing 13.0 g of 4'-phenylphenyl 4-propen-2-oxy-benzoate, 10.9 g of cholestery 4-propen-2-oxy-benzoate, 2.3 g of 4-(4-propen-2-oxy-benzylideneamino)-azobenzene and 4.0 g of tetramethylcyclotetrasiloxane in 70 ml of toluene, and the resultant mixture was refluxed for 5 hours. In order to separate the platinum-containing fine precipitates, the mixture was filtered through a short column filled with silica gel. The solvent was subsequently removed by distillation at reduced pressure, and the residue was recrystallized several times from ethanol and dried at 60° C. at reduced pressure. About 21.3 g of a product having a glass transition temperature of 50° C. and having a cholesteric phase up to the clear point of 192° C. were obtained. In the oriented state, the product has a reflection maximum at 750 nm, while the absorption band of the chromophoric group is at 396 nm.

An oriented layer of the product on paper was obtained by drawing the paper over a heated surface and applying the product, heated to close to the clear point, in a layer 0.005 mm to 0.2 mm thick by means of a hand coater oriented transversely to the drawing direction. The orientation of the liquid-crystalline layer is apparent from the appearance of the reflection color typical of such liquid crystals.

EXAMPLE 2

About 2.5 ml of a 1 percent by weight solution of dicyclopentadiene-platinum dichloride in dichloromethane were added to a solution containing 50.0 g of 4'-phenylphenyl 4-propen-2-oxy-benzoate, 74.6 g of cholesteryl 4-propen-2-oxy-benzoate, 3.6 g of 4-(4-propen-2-oxy)azobenzene and 18.1 g of a polymethylhydrogensiloxane having a viscosity of 24 MPa.s at 25° C. in 350 ml of toluene, and the resultant mixture was refluxed for 5 hours. The solvent was subsequently removed by distillation at 60° C. at reduced pressure, and the product was isolated and purified in accordance with the procedure described in Example 1. About 121.3 g of a product were obtained which has a glass transition temperature of 56° C., exists in a smectic phase up to 164° C., is cholesteric above this temperature and has a clear point at 224° C. In the cholesteric state, the product can easily be oriented by shearing, and in the orientated state, has a reflection maximum of 680 nm. On rapid cooling to below the glass transition temperature, a metastable cholesteric phase was obtained.

What is claimed is:

1. A cholesterically liquid-crystalline organopolysiloxane which contains, in the side groups, both non-chromophoric mesogens, at least some of which are optically active, and chromophoric groups.

2. The organopolysiloxane of claim 1 which contains azo or azoxy groups as the chromophoric groups.

3. The organopolysiloxane of claim 2, which is built up from units of the formula

$$R_aR'_bR''_cSiO_{(4-a-b-c)/2}. \quad (I)$$

where R represents monovalent radicals of the formula

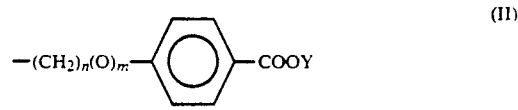

in which n represents an integer having a value of from 2 to 12, m represents an integer having a value of 0 or 1, and Y represents radicals selected from the group consisting of (i) phenyl radicals which are substituted in the para-position by groups selected from the group consisting of halogen, cyano, $C_1$- to $C_8$-alkoxy, phenyl, phenoxy and cyclohexyl radicals and (ii) radicals selected from the group consisting of cholesteryl, 4-cyclohexyl-cyclohexyl and pinan-10-yl radicals; R' represents monovalent radicals of the formula

$$-(CH_2)_n(O)_m-Z \quad (III)$$

in which n and m are the same as above and Z is a radical selected from the formula consisting of

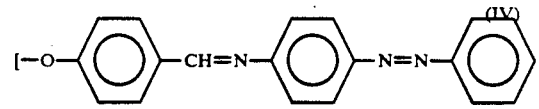

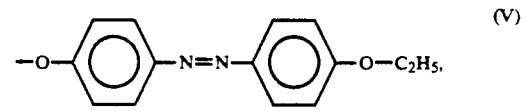

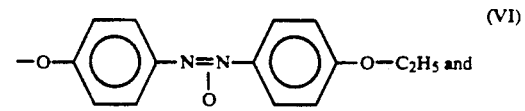

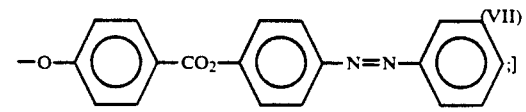

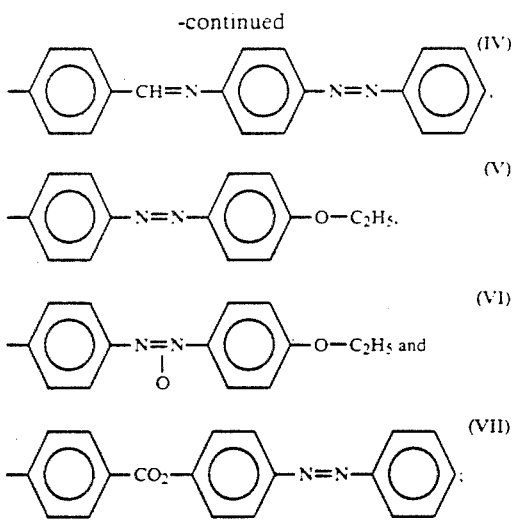

R″ represents radicals selected from the group consisting of $C_1$- to $C_8$-alkyl radicals and the phenyl radical, which may optionally be substituted by halogen atoms, and a, b and c each represent integers having a value of from 0 to 3, with the proviso that the sum of a, b and c is a maximum of 3, and on the average, each organopolysiloxane molecule contains at least one unit of formula (I) in which a has a value of at least 1 and one unit in which b has a value of at least 1.

4. The organopolysiloxane of claim 3, which is built up of units of formulas $$R_aR''_cSiO_{(4-a-b-c)/2} \qquad (VIII)$$

$$R'_bR''_cSiO_{(4-a-b-c)/2} \qquad (IX)$$

and optionally $$R''_cSiO_{4-c/2} \qquad (X)$$

in which R represents monovalent radicals of the formula

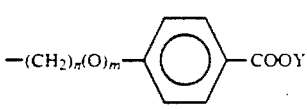

in which n represents an integer having a value of from 2 to 12, m represents an integer having a value of 0 or 1, and Y represents radicals selected from the group consisting of (i) phenyl radicals which are substituted in the para-position by groups selected from the group consisting of halogen, cyano, $C_1$- to $C_8$-alkoxy, phenyl, phenoxy and cyclohexyl radicals and (ii) radicals selected from the group consisting of cholesteryl, 4-cyclohexyl-cyclohexyl and pinan-10-yl radicals; R' represents monovalent radicals of the formula $$-(CH_2)_n(O)_m-Z \qquad (III)$$

in which n and m are the same as above and Z is a radical selected from the formula consisting of

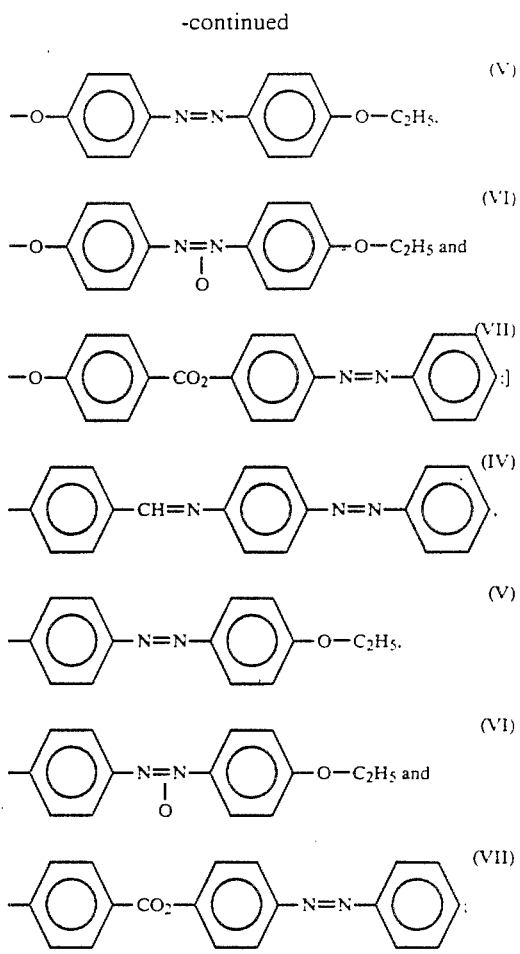

R″ represents selected from the group consisting of $C_1$- to $C_8$-alkyl radicals and the phenyl radical, which may optionally be substituted by halogen atoms, and a, b and c each represent integers having a value of from 0 to 3, with the proviso that the sum of a, b and c is a maximum ob 3, and on the average, each organopolysiloxane molecule contains at least one unit of formula (I) in which a has a value of at least 1 and one unit in which b has a value of at least 1.

5. The organopolysiloxane of claim 3 in which R″ is selected from the group consisting of methyl, ethyl and phenyl radicals, and the sum of a+b+c in each case has an average value of from 1.8 to 2.2.

6. The organopolysiloxane of claim 4, in which R″ is selected from the group consisting of methyl, ethyl and phenyl radicals, and the sum of a+b+c in each case has an average value of from 1.8 to 2.2.

7. The organopolysiloxane of claim 1, which has a weight average molecular weight of at least 1,200.

8. The organopolysiloxane of claim 2, which has a weight average molecular weight of at least 1,200.

9. The organopolysiloxane of claim 3, which has a weight average molecular weight of at least 1,200.

10. The organopolysiloxane of claim 4, which has a weight average molecular weight of at least 1,200.

11. The organopolysiloxane of claim 5, which has a weight average molecular weight of at least 1,200.

12. The organopolysiloxane of claim 6, which has a weight average molecular weight of at least 1,200.

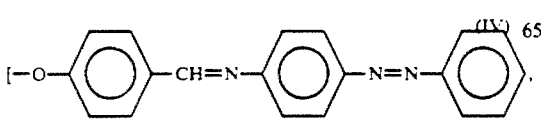

13. A process for preparing the organopolysiloxane of claim 1 in which an organopolysiloxane of the formula

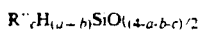

is reacted with a compound of the formula

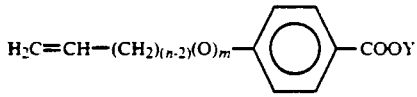

and a compound of the formula $H_2C=CH-(CH_2)_{(n-2)}(O)_m-Z$ (XIII)

in which R" represents radicals selected from the group consisting of $C_1$- to $C_8$-alkyl radicals and a phenyl radical, which may optionally be substituted by halogen atoms, Y represents radicals selected from the group consisting of phenyl radicals which are substituted in the para-position by groups selected from halogen, cyano, $C_1$- to $C_8$-alkoxy, phenyl, phenoxy or cyclohexyl radicals and radicals selected from the group consisting of cholesteryl, 4-cyclohexyl-cyclohexyl and pinan-10-yl radicals; Z is a radical selected from the formulas consisting of

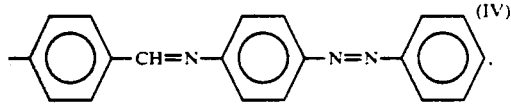

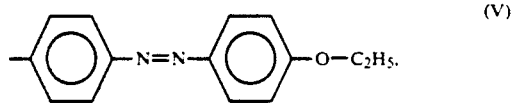

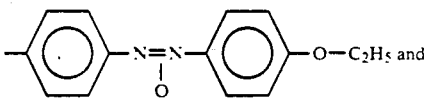

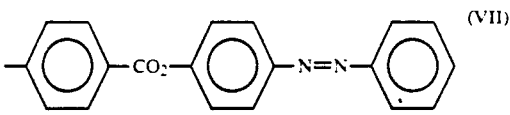

a, b and c each represent integers having a value of from 0 to 3, with the proviso that the sum of a+b+c is a maximum of 3, and on the average, a and b have a value of at least 1; n represents an integer having a value of from 2 to 12; m represents an integer having a value of 0 or 1, in the presence of a platinum metal and/or a compound thereof.

14. An information storage device containing the organopolysiloxane of claim 1.

15. An information storage device containing the organopolysiloxane of claim 2.

16. An information storage device containing the organopolysiloxane of claim 3.

17. An information storage device containing the organopolysiloxane of claim 4.

18. An information storage device containing the organopolysiloxane of claim 5.

19. An information storage device containing the organopolysiloxane of claim 6.

20. An information storage device containing the organopolysiloxane of claim 7.

21. An information storage device containing the organopolysiloxane of claim 8.

22. An information storage device containing the organopolysiloxane of claim 9.

23. An information storage device containing the organopolysiloxane of claim 10.

24. An information storage device containing the organopolysiloxane of claim 11.

25. An information storage device containing the organopolysiloxane of claim 12.

26. An information storage device containing the organopolysiloxane produced by the process of claim 13.

* * * * *

UNITED STATES PATENT AND TRADEMARK OFFICE
CERTIFICATE OF CORRECTION

PATENT NO. : 5,098,978

DATED : March 24, 1992

INVENTOR(S) : Georg Riepl, Franz-Heinrich Kreuzer and Alfred Miller

It is certified that error appears in the above-identified patent and that said Letters Patent is hereby corrected as shown below:

Please delete :
Column 6, lines  50 through 66 and

Column 7, lines 65 to 68 and column 8, lines 1 through 15

Signed and Sealed this

Twenty-second Day of June, 1993

Attest:

MICHAEL K. KIRK

*Attesting Officer*  *Acting Commissioner of Patents and Trademarks*